United States Patent [19]

Kubo et al.

[11] Patent Number: 4,873,375
[45] Date of Patent: Oct. 10, 1989

[54] PROCESS FOR PREPARING FLUORINE-SUBSTITUTED ALICYCLIC DIOL

[75] Inventors: Motonobu Kubo; Yoshiki Shimizu, both of Osaka, Japan

[73] Assignee: Daikin Industries, Ltd., Osaka, Japan

[21] Appl. No.: 180,118

[22] Filed: Apr. 11, 1988

[30] Foreign Application Priority Data

Apr. 11, 1987 [JP] Japan .................................. 62-89283

[51] Int. Cl.$^4$ ............................................. C07C 33/44
[52] U.S. Cl. ................................... 568/812; 568/811; 568/832
[58] Field of Search ............... 568/832, 812, 835, 814, 568/811

[56] References Cited

U.S. PATENT DOCUMENTS

| | | | |
|---|---|---|---|
| 1,771,089 | 7/1930 | Jordan | 568/832 |
| 2,328,719 | 9/1943 | Houghton et al. | 568/832 |
| 2,574,077 | 11/1951 | Whitaker et al. | 568/834 |
| 2,927,127 | 4/1960 | Somerville et al. | 58/834 |
| 3,067,915 | 1/1978 | Yashara et al. | 568/832 |
| 4,551,564 | 11/1985 | Otte et al. | 568/834 |

FOREIGN PATENT DOCUMENTS

| | | | |
|---|---|---|---|
| 0059649 | 5/1978 | Japan | 568/835 |
| 0090242 | 8/1978 | Japan | 568/835 |

Primary Examiner—Werren B. Lone
Attorney, Agent, or Firm—Birch, Stewart, Kolasch & Birch

[57] ABSTRACT

A process for preparing a fluorine-substituted alicyclic diol comprising hydrogenating in the presence of a catalyst a fluorine-substituted aromatic diol represented by formula (I):

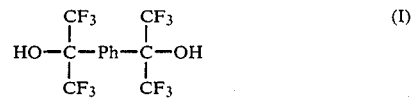

wherein Ph represents a divalent organic group containing at least one aromatic group, to obtain the fluorine-substituted alicyclic diol represented by formula (II):

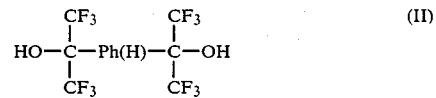

wherein Ph(H) represents a divalent organic group containing at least one perhydroaromatic group.

10 Claims, No Drawings

PROCESS FOR PREPARING FLUORINE-SUBSTITUTED ALICYCLIC DIOL

BACKGROUND OF THE INVENTION

1. Field of the Invention

The present invention relates to a process for preparing a fluorine-substituted alicyclic diol. The diol is used as a starting material for epoxy resins, polyurethane resins, polyester resins, and the like, which are characterized with excellent properties of heat resistance, water resistance, tracking resistance, weather resistance, and the like. These resins are used as adhesives, vehicles of paints, packing materials for electronic devices, etc.

2. Discussion of Related Art

It is disclosed that bis(1,1,1,3,3,3-hexafluoro-2-hydroxyisopropyl)cyclohexane, a representative example of fluorine-substituted alicyclic diols, is prepared by a process in which hexafluoroacetone is free-radically added to cyclohexane in *J. Am. Chem. Soc.*, vol. 89. pages 1422 to 1430 (1967). However, the period of time required for completing the reaction by this process is considerably long, and the yield is low, because of by-products such as cyclohexyl 1,1,1,3,3,3-hexafluoroisopropyl ether, 1,1,1,3,3,3-hexafluoro-2-cyclohexyl-2-propanol and the like, being generate in a large amount.

SUMMARY OF THE INVENTION

Therefore, an object of the present invention is to provide a novel process for preparing a fluorine-substituted alicyclic diol.

Another object of the present invention is to provide a process for preparing a fluorine-substituted alicyclic diol in which the fluorine-substituted alicyclic diol can be obtained in a short period of time and in a high yield, and with only a small amount of by-products being generated.

Other objects of the present invention will be apparent from the following description.

It has been found that the above objects of the present invention can be achieved by a process for preparing a fluorine-substituted alicyclic diol comprising hydrogenating in the presence of a catalyst a fluorine-substituted aromatic diol represented by formula (I):

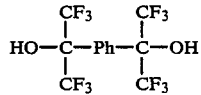
(I)

wherein Ph represents a divalent organic group containing at least one aromatic group, to obtain the fluorine-substituted alicyclic diol represented by formula (II):

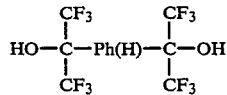
(II)

wherein Ph(H) represents a divalent organic group containing at least one perhydroaromatic group.

DETAILED DESCRIPTION OF THE INVENTION

The present invention will be described in more detail below.

Examples of the divalent organic group represented by Ph include a phenylene group, a biphenylene group, a terphenylene group, a phenyleneoxyphenylene group, a phenylenethiophenylene group a phenylenealkylenephenylene group, an anthrylene group, and a phenanthrylene group, a hydrogen atom of which may be substituted by a methyl group, a hydroxyl group, an amino group, or a halogen atom such as a chlorine atom and a fluorine atom. The alkylene group contained in the above groups has from 1 to 10 carbon atoms.

Examples of the divalent organic group represented by Ph(H) include a perhydrophenylene group, a perhydrobiphenylene group, a perhydroterphenylene group, a perhydrophenyleneoxyphenylene group, a perhydrophenylenethiophenylene group, a perhydrophenylenealkylenephenylene group, a perhydroperhydroanthrylene group, and a perhydrophenanthrylene group, a hydrogen atom of which may be substituted by a methyl group, a hydroxyl group, an amino group, or a halogen atom such as a chlorine atom and a fluorine atom. The alkylene group contained in the above groups has from 1 to 10 carbon atoms.

Specific examples of the aromatic diol represented by formula (I) include the following compound, but the present invention is not intended to be limited thereto.

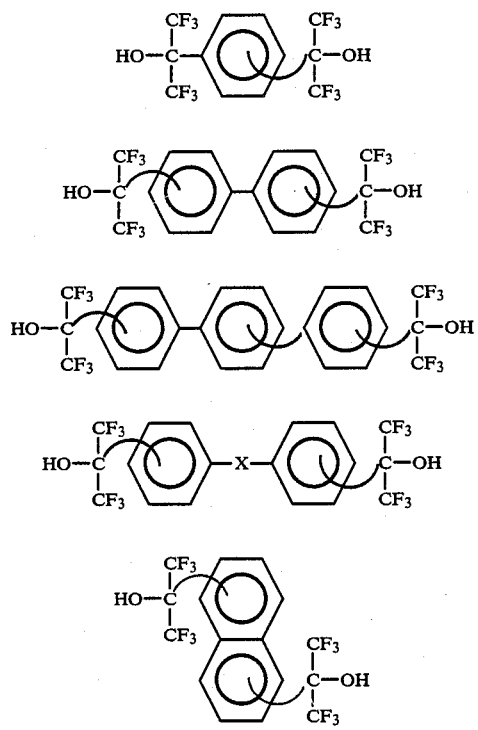

-continued

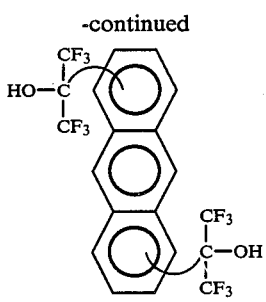

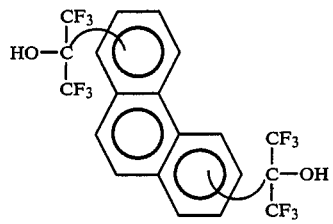

In the above compounds, X represents an oxygen atom, a sulfur atom, or an alkylene group having from 1 to 10 carbon atoms.

These aromatic diol represented by formula (I) can be prepared by any known method, e.g., by addition reaction of hexafluoroacetone to an aromatic hydrocarbon, such as benzene, naphthalene, biphenyl, etc., at 40 to 50° C. in the presence of anhydrous aluminum chloride, as described in *J. Org. Chem.*, vol. 30, pages 998 to 1001 (1965).

The group

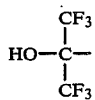

may be connected to any position of the aromatic nuclei, and another hydrogen atoms in the aromatic nuclei may further be substituted by a methyl group, a hydroxyl group, an amino group, a halogen atom, such as a chlorine atom and a fluorine atom, etc. in addition to the above-mentioned fluorine-containing group.

By the hydrogenating reaction according to the present invention, the following compounds can also be hydrogenated as well as the aromatic diol represented by formula (I).

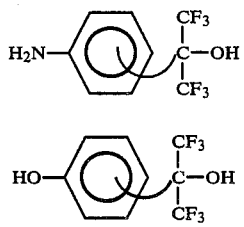

In the process according to the present invention, the catalysts are those which are generally used in the conventional hydrogenating reaction. Examples of these catalysts include rhodium, ruthenium, palladium, platinum, etc. Among these catalysts, rhodium is most preferred in view of its high reaction rate. The metals of the catalysts used are preferably in the form of oxides as well as simple substances. In addition to the above metals, a Raney nickel catalyst may be used.

The catalyst is generally supported on a carrier in an amount of from 0.01 to 30 wt% based on the total amount of the catalyst and the carrier. Examples of the carrier include activated carbon, alumina, zeolite, etc.

In practice of the process according to the present invention, the catalyst is preferably used in an amount of from 0.001 to 20 wt% based on the amount of the aromatic diol.

The reaction of the process according to the present invention is generally carried out at a temperature range of from 10 to 250° C., and preferably from 50 to 200° C.; and the process does not depend on the hydrogen pressure and but is carried out generally under a hydrogen pressure of from 1 to 250 kg/cm²G, and preferably from 10 to 150 kg/cm²G.

A solvent can be used in the process according to the present invention. Alcohols are generally used as the solvent. Preferred examples of the solvent include methanol, ethanol, n-propanol, isopropanol, n-butanol, etc. The solvent is preferably used in an amount of from the same weight as the weight of the aromatic diol to 30 times the weight of the aromatic diol.

After completion of the hydrogenating reaction, the objective compound (i.e., a fluorine-substituted alicyclic diol) can be isolated by filtering off the catalyst and then applying conventional isolation techniques such as distillation, recrystallization, or column chromatography.

By the hydrogenating reaction according to the present invention, a fluorine-substituted alicyclic diol represented by formula (II) is obtained:

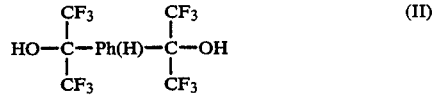

wherein Ph(H) represents a divalent organic group containing at least one perhydroaromatic group.

Specific examples of the alicyclic diol represented by formula (II) include the following compound, but the present invention is not intended to be limited thereto.

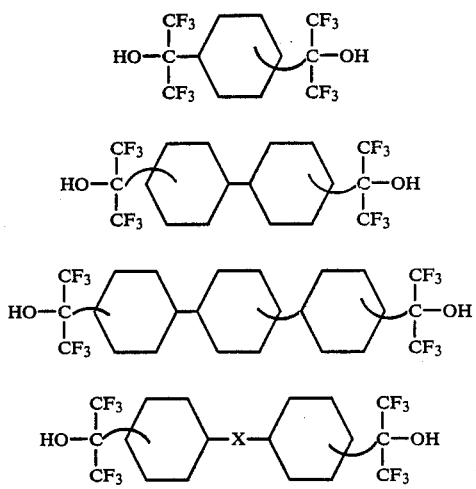

-continued

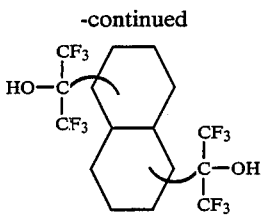

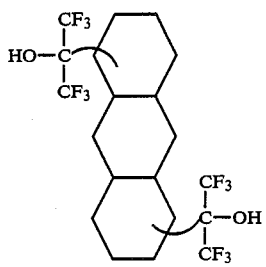

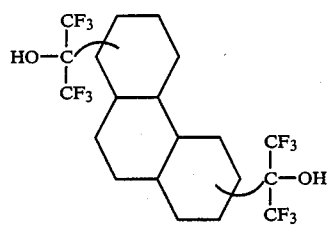

In the above compounds, X represents an oxygen atom, a sulfur atom, or an alkylene group having from 1 to 10 carbon atoms.

The group

may be connected to any position of the perhydroaromatic nuclei, and another hydrogen atoms in the perhydroaromatic nuclei may further be substituted by a methyl group, a hydroxyl group, an amino group, a halogen atom, such as a chlorine atom and a fluorine atom, etc. in addition to the above-mentioned fluorine-containing group.

By the hydrogenating reaction according to the present invention, the following compounds can also be prepared as well as the alicyclic diol represented by formula (II).

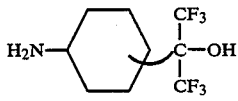

The present invention will be explained in more detail below by referring to the examples, but the present invention is not intended to be limited thereto. Unless indicated specifically, all ratios, percents, and the like are by weight.

EXAMPLE 1

Preparation of bis(1,1,1,3,3,3-hexafluoro-2-hydroxyisopropyl)benzene 117 g (1.5 mol) of benzene and 31 g (0.23 mol) of anhydrous aluminum chloride were placed in a 1l-flask equipped with a stirrer, and 500 g (3 mol) of hexafluoroacetaone was added thereto in an addition rate of about 5 g/minute at room temperature.

After the completion of the addition, the reaction mixture was distilled under reduced pressure to obtain 517 g (1.26 mol) of bis(1,1,1,3,3,3-hexafluoro 2-hydroxyisopropyl)benzene having a meta-isomer/para-isomer ratio of 85/15 (b.p.: 102–106° C./20mmHg). The yield based on the starting hexafluoroacetaone was 84%.

Preparation of bis(1,1,1,3,3,3-hexafluoro-2-hydroxyisopropyl)cyclohexane

A mixture of 300 g (0.73 mol) of the above-prepared bis(1,1,1,3,3,3-hexafluoro-2-hydroxyisopropyl)benzene and 300 ml of isopropanol was placed in an autoclave made of Hastelloy (trademark of a heat resistant nickel alloy made by Haynes Stellite Co.), and then 30 g of activated carbon carrying catalyst of rhodium in an amount of 5 wt% based on the total amount of the catalyst and the activated carbon was added thereto. The mixture was heated to 155° C. while stirring, and then hydrogen was blown into the mixture at the substantially same temperature under a hydrogen pressure of 60 kg/cm²G for 4.5 hours.

After the completion of the reaction, the reaction mixture was cooled to room temperature. Then, the catalyst was filtered off, and the filtrate was distilled to remove the isopropanol and to obtain 287 g (0.69 mol) of bis(1,1,1,3,3,3-hexafluoro-2-hydroxyisopropyl)cyclohexane (b.p.: 96–100° C./6mmHg). The yield based on the amount of bis (1,1,1,3,3,3-hexafluoro-2-hydroxyisopropyl)-benzene was 94%.

Results of $^1$H-NMR (nuclear magnetic resonance) (solvent: carbon tetrachloride) analysis were as follows: $\delta$(ppm) =3.1 (2H, s, OH), 1.1–2.5 (10H, br, CH or CH$_2$)

EXAMPLE 2

The same procedures as in Example 1 were repeated except that the amount of activated carbon carrying the catalyst was changed to 15 g, the reaction temperature was changed to 160° C., and the reaction time was changed to 9 hours. As a result, 282 g of bis(1,1,1,3,3,3-hexafluoro-2-hydroxyisopropyl)cyclohexane was obtained.

EXAMPLES 3 to 5

The same procedures as in Example 1 were repeated except that the rhodium as the catalyst was changed to ruthenium (Example 3), palladium (Example 4), and platinun (Example 5) to obtain bis(1,1,1,3,3,3-hexafluoro-2hydroxyisopropyl)cyclohexane. The yields in Examples 3 to 5 were 29 g (9.5%), 44 g (14%), and 85 g (28%), respectively.

COMPARATIVE EXAMPLE 1

63 (0.75 mol) of cyclohexane, 246 g (1.48 mol) of hexafluoroacetaone, and 1.46 g (0.01 mol) of di-tert-butylperoxide were placed in an autoclave made of Hastelloy, and the mixture was stirred for 8 hours at 135° C. After cooling, 1.46 g (0.01 mol) of di-tertbutylperoxide was added thereto while applying pressure, and the mixture was stirred for 8 hours at 135° C. The procedures after cooling step were repeated 10 times in total.

After the completion of the reaction, the reaction mixture was distilled to obtain 141 g of objective bis(1,1,1,3,3,3-hexafluoro-2-hydroxyisopropyl)cyclohexane. The yield based on the amount of the starting hexafluoroacetaone was 46%. Additionally, 10 g of cyclohexyl-1,1,1,3,3,3-hexafluoroisopropyl ether (b.p.: 50-54° C./23mmHg) and 62 g of 1,1,1,3,3,3-hexafluoro-2-cyclohexyl-2-propanol (b.p.: 65-67° C./23mmHg) were formed as major by-products.

From the results shown in the foregoing, it is understood that a fluorine-substituted alicyclic diol can be prepared in a short period of time and in a high yield by the process according to the present invention. Such effects of the present invention become more significant in the case where rhodium is used as the catalyst.

While the present invention has been described in detail and with reference to specific examples thereof, it will be apparent to one skilled in the art that various changes and modifications can be made therein without departing from the spirit and scope thereof.

What is claimed is:

1. A process for preparing a fluorine-substituted alicyclic diol comprising reacting a fluorine-substituted aromatic diol represented by formula (I):

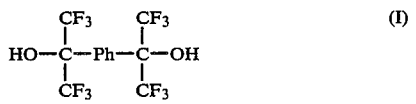
(I)

wherein Ph represents a divalent organic group selected from the group consisting of a phenylene group, a biphenylene group, a terphenylene group, a phenyleneoxy-phenylene group, a phenylenethiophenylene group, a phenylenealkylenephenylene group, an anthrylene group, a phenanthrylene group and said divalent organic group or which at least one hydrogen atom of said group is substituted by a methyl group, a hydroxyl group, an amino group or a halogen atom, in which the alkylene group contained in said group represented by Ph has from 1 to 10 carbon atoms with hydrogen in the presence of a rhodium catalyst;
   at a temperature in the range of from 10° to 250° C. under a hydrogen pressure in the range of from 1 to 250 kg/cm² G;
   to obtain said fluorine-substituted alicyclic diol represented by formula (II):

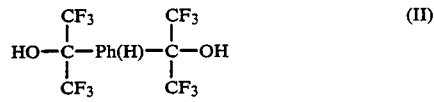
(II)

wherein Ph(H) represents the corresponding fully hydrogenated Ph group.

2. The process according to claim 1, wherein said rhodium catalyst is in the form of a simple substance or an oxide.

3. The process according to claims 1 or 2, wherein said rhodium catalyst is supported on a carrier selected from the group consisting of activated carbon, alumina and zeolite in an amount of from 0.01 to 30 wt % based on the total amount of said catalyst and said carrier.

4. The process according to claims 1 or 2, wherein said rhodium catalyst is used in an amount of from 0.001 to 20 wt % based on the amount of said fluorine-substituted aromatic diol.

5. The process according to claims 1 or 2, wherein the reaction temperature is in the range of from 50° to 200° C.

6. The process according to claims 1 or 2, wherein the hydrogen pressure of said reaction is in the range of from 10 to 150 kg/cm² G.

7. The process according to claim 3, wherein reaction temperature is in the range of from 50° to 200° C.

8. The process according to claim 4, wherein the reaction temperature is in the range of from 50° to 200° C.

9. The process according to claim 3, wherein the hydrogen pressure of said reaction is in the range of from 10 to 150 kg/cm² G.

10. The process according to claim 4, wherein the hydrogen pressure of said reaction is in the range of from 10 to 150 kg/cm² G.

* * * * *